(12) United States Patent
Perot et al.

(10) Patent No.: US 10,195,112 B2
(45) Date of Patent: Feb. 5, 2019

(54) ADAPTOR FOR MULTIDOSE MEDICAL CONTAINER

(71) Applicant: Becton Dickinson France, Le Pont de Claix (FR)

(72) Inventors: Frederic Perot, Saint Paul de Varces (FR); Adrien Plouvier, Saint Martin D'Heres (FR); Anick Lagier, Saint Paul de Varces (FR)

(73) Assignee: Becton Dickinson France, Le Pont de Claix (FR)

( * ) Notice: Subject to any disclaimer, the term of this patent is extended or adjusted under 35 U.S.C. 154(b) by 235 days.

(21) Appl. No.: 14/647,196

(22) PCT Filed: Nov. 25, 2013

(86) PCT No.: PCT/EP2013/074545
§ 371 (c)(1),
(2) Date: May 26, 2015

(87) PCT Pub. No.: WO2014/080002
PCT Pub. Date: May 30, 2014

(65) Prior Publication Data
US 2015/0320639 A1    Nov. 12, 2015

(30) Foreign Application Priority Data
Nov. 26, 2012 (EP) .................................. 12306460

(51) Int. Cl.
*A61J 1/18* (2006.01)
*A61J 1/14* (2006.01)
*A61J 1/20* (2006.01)

(52) U.S. Cl.
CPC ............... *A61J 1/18* (2013.01); *A61J 1/1406* (2013.01); *A61J 1/1412* (2013.01); *A61J 1/2055* (2015.05); *A61J 1/2096* (2013.01); *A61J 1/2058* (2015.05); *A61M 2205/583* (2013.01)

(58) Field of Classification Search
CPC ...... A61J 1/1412; A61J 1/2058; A61J 1/1406; A61J 1/20; A61J 1/2096; A61M 2205/583
See application file for complete search history.

(56) References Cited

U.S. PATENT DOCUMENTS

| 2,459,304 A | 1/1949 | Blank |
| 2,629,379 A | 2/1953 | Fields |
| 3,392,726 A | 7/1968 | Pochyla et al. |
| 3,768,474 A | 10/1973 | Burke et al. |

(Continued)

FOREIGN PATENT DOCUMENTS

| DE | 10127823 C1 | 8/2002 |
| DE | 102008060864 A1 | 6/2010 |

(Continued)

*Primary Examiner* — Leslie Deak
(74) *Attorney, Agent, or Firm* — The Webb Law Firm

(57) ABSTRACT

An adaptor for coupling with a medical container filled with a number N of doses of a product including a gripping member for securing the adaptor to the medical container. The gripping member has at least one needle access port intended to face the outer surface of the septum of the medical container. The adaptor also includes a marking-device coupled to the needle access port, for designating to a user a not yet pierced area of said outer surface, for completing the next of the N successive piercings.

19 Claims, 6 Drawing Sheets

(56) References Cited

U.S. PATENT DOCUMENTS

| | | |
|---|---|---|
| 3,884,229 A | 5/1975 | Raines et al. |
| 3,940,003 A | 2/1976 | Larson |
| 3,976,073 A | 8/1976 | Quick et al. |
| 3,995,630 A | 12/1976 | van de Veerdonk |
| 4,128,098 A | 12/1978 | Bloom et al. |
| 4,338,980 A | 7/1982 | Schwebel et al. |
| 4,592,742 A | 6/1986 | Landau |
| 4,723,955 A | 2/1988 | Vaillancourt |
| 4,786,281 A | 11/1988 | Valentini et al. |
| 4,821,996 A | 4/1989 | Bellotti et al. |
| 5,017,186 A | 5/1991 | Arnold |
| 5,024,256 A | 6/1991 | Vadher |
| 5,060,704 A | 10/1991 | Rohrbough |
| 5,102,406 A | 4/1992 | Arnold |
| 5,125,921 A | 6/1992 | Duschek |
| 5,329,976 A | 7/1994 | Haber et al. |
| 5,342,319 A | 8/1994 | Watson et al. |
| 5,454,409 A | 10/1995 | McAffer et al. |
| 5,498,253 A | 3/1996 | Aswad et al. |
| 5,527,306 A | 6/1996 | Haining |
| 5,533,996 A | 7/1996 | Murphey et al. |
| 5,678,718 A | 10/1997 | Morris et al. |
| 5,716,346 A | 2/1998 | Farris |
| 5,772,652 A | 6/1998 | Zielinski |
| 5,776,124 A | 7/1998 | Wald |
| 5,893,397 A | 4/1999 | Peterson et al. |
| 5,924,584 A | 7/1999 | Hellstrom et al. |
| 6,006,798 A | 12/1999 | Lindquist |
| 6,258,078 B1 | 7/2001 | Thilly |
| 6,277,091 B1 | 8/2001 | Genet |
| 6,364,866 B1 | 4/2002 | Furr et al. |
| 6,453,956 B2 | 9/2002 | Safabash |
| 6,599,273 B1 | 7/2003 | Lopez |
| 6,685,693 B1 | 2/2004 | Casso |
| 6,755,220 B2 | 6/2004 | Castellano et al. |
| 6,755,810 B1 | 6/2004 | Buch-Rasmussen et al. |
| 6,880,722 B2 | 4/2005 | Anderson et al. |
| 7,029,465 B2 | 4/2006 | Heyes et al. |
| 7,100,646 B2 | 9/2006 | Py et al. |
| 7,382,692 B1 | 6/2008 | Hildebrandt |
| 7,425,207 B2 | 9/2008 | Miller et al. |
| 7,488,311 B2 | 2/2009 | Domkowski et al. |
| 7,491,197 B2 | 2/2009 | Jansen et al. |
| 7,530,974 B2 | 5/2009 | Domkowski et al. |
| 7,547,300 B2 | 6/2009 | Fangrow |
| 7,559,321 B2 | 7/2009 | Wermeling et al. |
| 7,575,567 B2 | 8/2009 | Simpkins |
| 7,621,273 B2 | 11/2009 | Morton et al. |
| 7,736,353 B2 | 6/2010 | Reynolds |
| 7,980,276 B2 | 7/2011 | Py |
| 8,002,130 B2 | 8/2011 | Thilly |
| 8,029,747 B2 | 10/2011 | Helmerson |
| 8,034,041 B2 | 10/2011 | Domkowski et al. |
| 8,034,042 B2 | 10/2011 | Domkowski et al. |
| 8,052,944 B2 | 11/2011 | Kacian et al. |
| 8,066,688 B2 | 11/2011 | Zinger et al. |
| 8,080,002 B2 | 12/2011 | Stergiopulos et al. |
| 8,090,471 B2 | 1/2012 | Shows et al. |
| 8,091,727 B2 | 1/2012 | Domkowski |
| 8,113,199 B2 | 2/2012 | Augustyn et al. |
| 8,122,923 B2 | 2/2012 | Kraus et al. |
| 8,157,784 B2 | 4/2012 | Rogers |
| 8,162,914 B2 | 4/2012 | Kraushaar et al. |
| 8,211,710 B2 | 7/2012 | Dickey et al. |
| 8,225,949 B2 | 7/2012 | Aneas |
| 8,303,572 B2 | 11/2012 | Adair et al. |
| 8,479,732 B2 | 7/2013 | Stuart et al. |
| 8,628,508 B2 | 1/2014 | Weitzel et al. |
| 8,763,798 B2 | 7/2014 | Paul |
| 8,839,971 B2 | 9/2014 | Aneas |
| 2002/0087144 A1 | 7/2002 | Zinger et al. |
| 2002/0121496 A1 | 9/2002 | Thiebault et al. |
| 2003/0071140 A1 | 4/2003 | Roman |
| 2004/0112855 A1* | 6/2004 | Becker .............. B29C 45/16 215/247 |
| 2004/0210207 A1 | 10/2004 | Amisar et al. |
| 2005/0055008 A1 | 3/2005 | Paradis et al. |
| 2005/0105014 A1 | 5/2005 | Hong |
| 2005/0113747 A1 | 5/2005 | Moir |
| 2005/0137523 A1 | 6/2005 | Wyatt et al. |
| 2005/0178462 A1 | 8/2005 | Py |
| 2008/0009789 A1 | 1/2008 | Zinger et al. |
| 2009/0050213 A1 | 2/2009 | Biddell et al. |
| 2009/0082750 A1 | 3/2009 | Denenburg et al. |
| 2009/0159485 A1 | 6/2009 | Jakob et al. |
| 2009/0314291 A1 | 12/2009 | Anderson et al. |
| 2009/0326506 A1 | 12/2009 | Hasegawa et al. |
| 2010/0022985 A1 | 1/2010 | Sullivan et al. |
| 2010/0059474 A1 | 3/2010 | Brandenburger et al. |
| 2010/0089862 A1 | 4/2010 | Schmitt |
| 2010/0168664 A1 | 7/2010 | Zinger et al. |
| 2010/0176080 A1* | 7/2010 | Grunert ............. B65D 41/3404 215/247 |
| 2010/0198148 A1 | 8/2010 | Zinger et al. |
| 2010/0204679 A1 | 8/2010 | Denenburg |
| 2010/0224632 A1 | 9/2010 | Aneas |
| 2011/0004183 A1 | 1/2011 | Carrez et al. |
| 2011/0022023 A1 | 1/2011 | Weitzel et al. |
| 2011/0073501 A1 | 3/2011 | Wu |
| 2011/0074148 A1 | 3/2011 | Imai |
| 2011/0083665 A1 | 4/2011 | Denton et al. |
| 2011/0098657 A1 | 4/2011 | Jennings |
| 2011/0098670 A1 | 4/2011 | Burnell |
| 2011/0125128 A1 | 5/2011 | Nord et al. |
| 2011/0144614 A1 | 6/2011 | Hereford |
| 2011/0245796 A1 | 10/2011 | Brandenburger et al. |
| 2011/0266249 A1 | 11/2011 | Kakutani et al. |
| 2012/0000569 A1 | 1/2012 | Wiegel |
| 2012/0223045 A1 | 9/2012 | Burke, Jr. |
| 2013/0204201 A1 | 8/2013 | Avery et al. |
| 2014/0163468 A1 | 6/2014 | Avery et al. |

FOREIGN PATENT DOCUMENTS

| | | |
|---|---|---|
| EP | 0176511 B1 | 9/1988 |
| EP | 0458543 A1 | 11/1991 |
| EP | 0499481 A1 | 8/1992 |
| EP | 0616510 A1 | 9/1994 |
| EP | 0706406 A1 | 4/1996 |
| EP | 0734708 A1 | 10/1996 |
| EP | 0748200 A1 | 12/1996 |
| EP | 0771184 A1 | 5/1997 |
| EP | 0783879 A2 | 7/1997 |
| EP | 0814866 A1 | 1/1998 |
| EP | 0836465 A1 | 4/1998 |
| EP | 0956849 A2 | 11/1999 |
| EP | 0959867 A1 | 12/1999 |
| EP | 0960616 A2 | 12/1999 |
| EP | 1034772 A1 | 9/2000 |
| EP | 1173286 A1 | 1/2002 |
| EP | 1323403 A1 | 7/2003 |
| EP | 1430864 A1 | 6/2004 |
| EP | 1631496 A2 | 3/2006 |
| EP | 1755520 A2 | 2/2007 |
| EP | 1797919 A1 | 6/2007 |
| EP | 1870347 A2 | 12/2007 |
| EP | 1971531 A1 | 9/2008 |
| EP | 2036529 A1 | 3/2009 |
| EP | 2059284 A1 | 5/2009 |
| EP | 2114344 A2 | 11/2009 |
| EP | 2133059 A2 | 12/2009 |
| EP | 2174884 A1 | 4/2010 |
| EP | 2190518 A2 | 6/2010 |
| EP | 2125548 B1 | 7/2010 |
| EP | 2134311 B1 | 10/2010 |
| EP | 2301510 A2 | 3/2011 |
| EP | 2306960 A2 | 4/2011 |
| EP | 2160337 B1 | 9/2011 |
| EP | 2262464 B1 | 10/2012 |
| EP | 2555814 A1 | 2/2013 |
| EP | 2383199 B1 | 6/2013 |
| EP | 2603260 A1 | 6/2013 |
| FR | 2847883 A1 | 6/2004 |
| FR | 2912384 A1 | 8/2008 |

(56) References Cited

FOREIGN PATENT DOCUMENTS

| | | | |
|---|---|---|---|
| GB | 2042137 | A | 9/1980 |
| GB | 2328432 | A | 2/1999 |
| GB | 2461086 | A | 12/2009 |
| JP | 2010531781 | A | 9/2010 |
| WO | 9311709 | A1 | 6/1993 |
| WO | 9501201 | A1 | 1/1995 |
| WO | 9523576 | A1 | 9/1995 |
| WO | 9600053 | A1 | 1/1996 |
| WO | 9629113 | A1 | 9/1996 |
| WO | 9640037 | A1 | 12/1996 |
| WO | 9832411 | A1 | 7/1998 |
| WO | 0035517 | A1 | 6/2000 |
| WO | 0234198 | A1 | 5/2002 |
| WO | 02056821 | A2 | 7/2002 |
| WO | 02102704 | A2 | 12/2002 |
| WO | 2004073775 | A1 | 9/2004 |
| WO | 2004096113 | A2 | 11/2004 |
| WO | 2005087127 | A1 | 9/2005 |
| WO | 2005105014 | A2 | 11/2005 |
| WO | 2007063218 | A1 | 6/2007 |
| WO | 2008020272 | A1 | 2/2008 |
| WO | 2008089948 | A2 | 7/2008 |
| WO | 2008153459 | A1 | 12/2008 |
| WO | 2009026443 | A2 | 2/2009 |
| WO | 2009038860 | A2 | 3/2009 |
| WO | 2009112535 | A1 | 9/2009 |
| WO | 2009153541 | A2 | 12/2009 |
| WO | 2010093581 | A3 | 8/2010 |
| WO | 2010099000 | A2 | 9/2010 |
| WO | 2010117580 | A1 | 10/2010 |
| WO | 2011007760 | A1 | 1/2011 |
| WO | 2011039747 | A1 | 4/2011 |
| WO | 2011045586 | A2 | 4/2011 |
| WO | 2011050333 | A1 | 4/2011 |
| WO | 2011060828 | A1 | 5/2011 |
| WO | 2011060829 | A1 | 5/2011 |
| WO | 2011124631 | A1 | 10/2011 |
| WO | 2012020083 | A1 | 6/2012 |

* cited by examiner

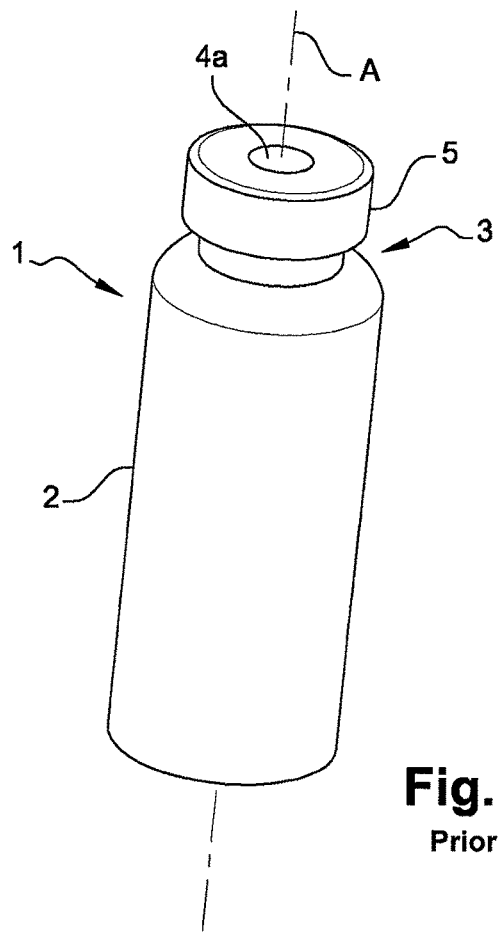
Fig. 1A
Prior Art
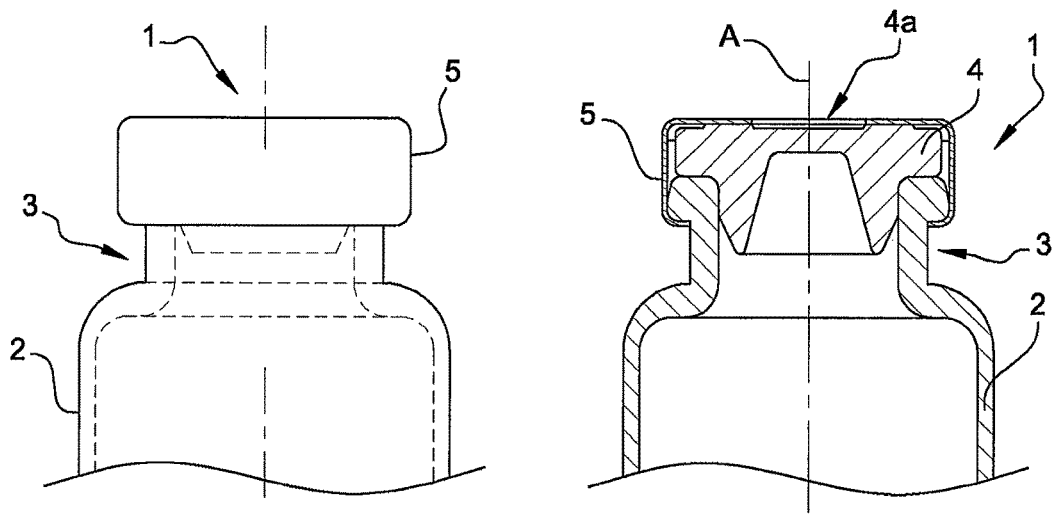
Fig. 1B
Prior Art
Fig. 1C
Prior Art

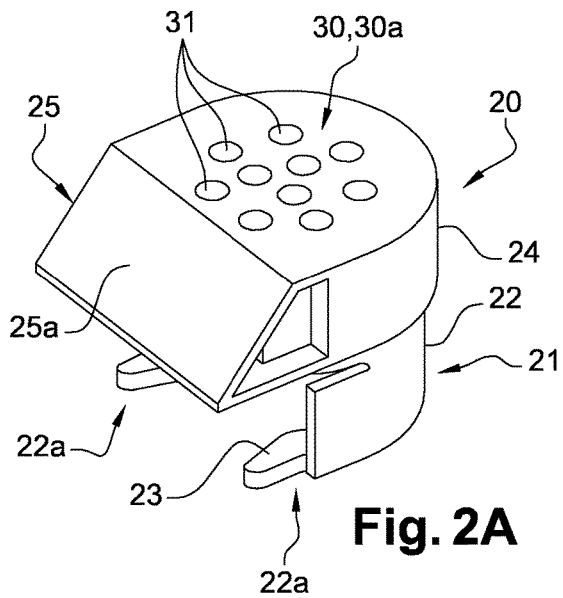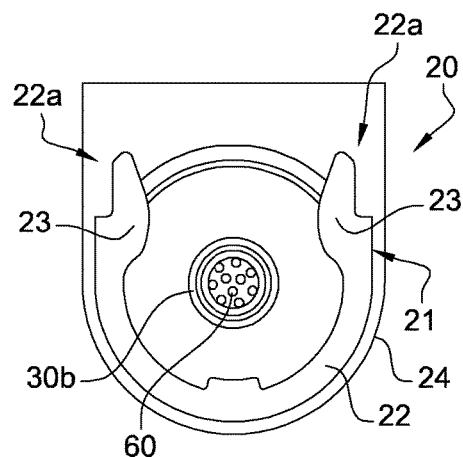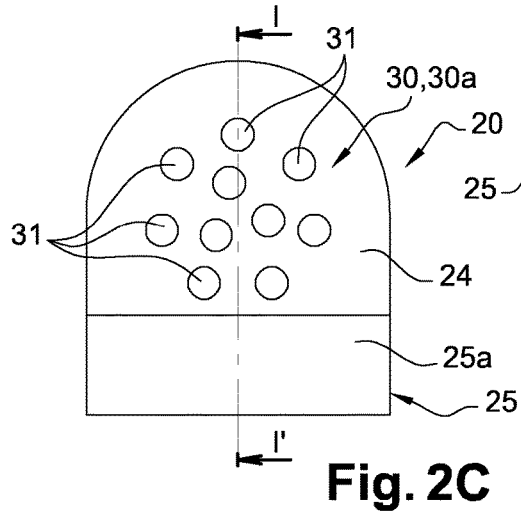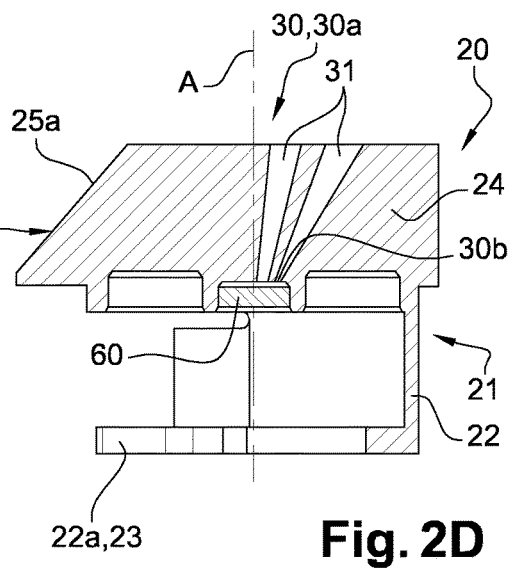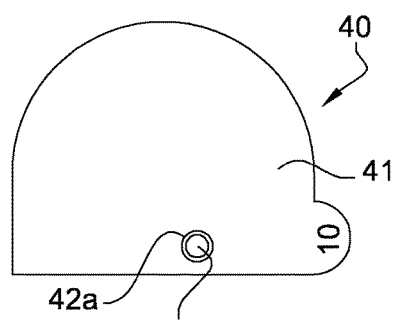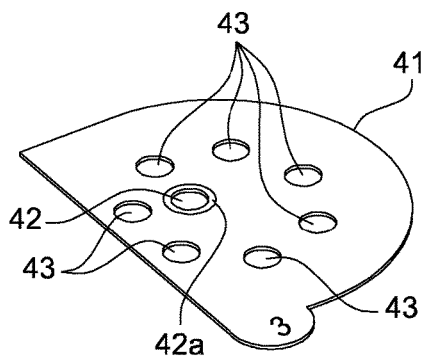

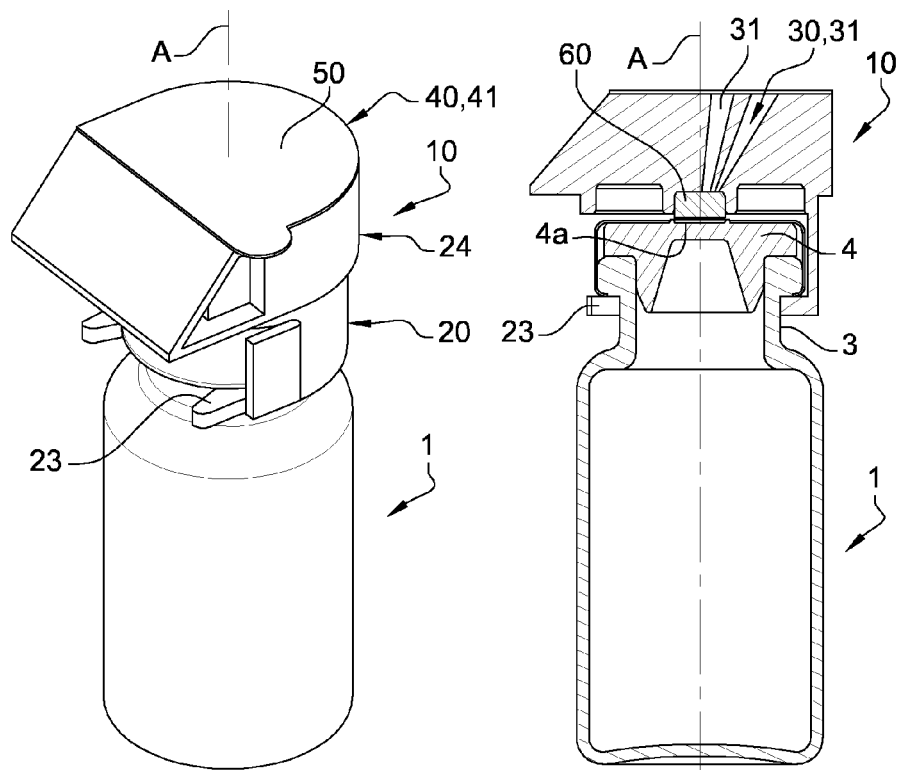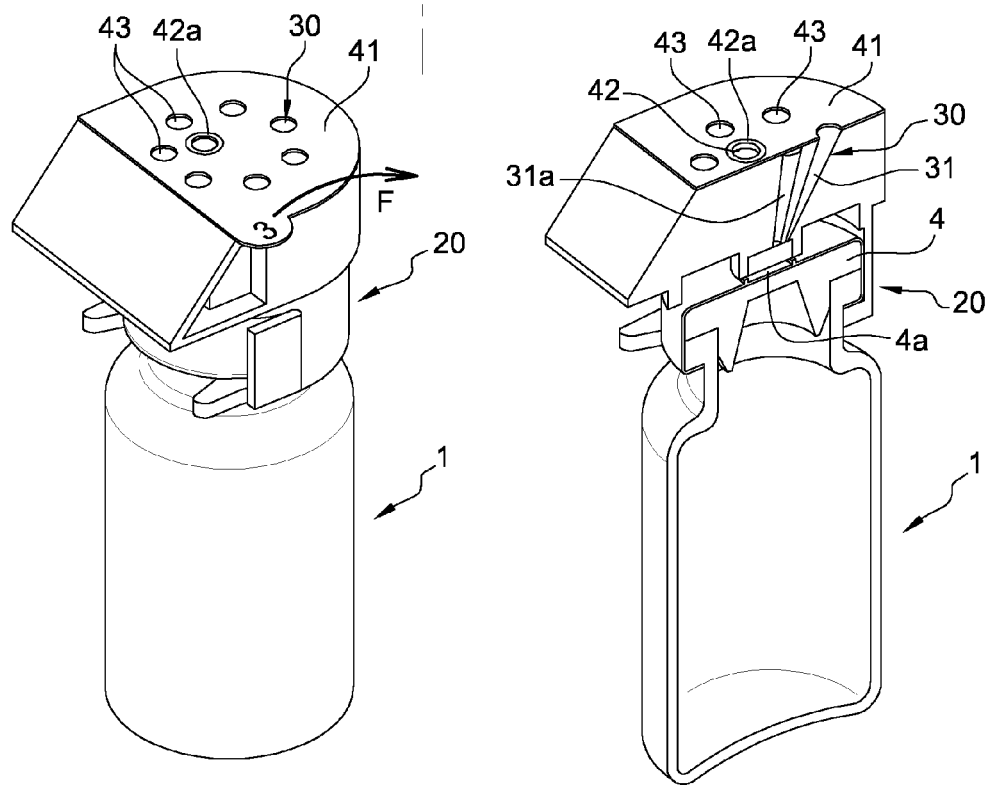
Fig. 4A    Fig. 4B
Fig. 5A    Fig. 5B

ADAPTOR FOR MULTIDOSE MEDICAL CONTAINER

CROSS-REFERENCE TO RELATED APPLICATIONS

This application is the United States national phase of International Application No. PCT/EP2013/074545 filed Nov. 25, 2013, and claims priority to European Patent Application No. 12306460.2 filed Nov. 26, 2012, the disclosures of which are hereby incorporated in their entirety by reference.

BACKGROUND OF THE INVENTION

Field of the Invention

The present invention relates to an adaptor for coupling to a medical container such as a vial containing a pharmaceutical product, such as a vaccine, said adaptor allowing for multiple aseptic needle piercings with an injection device to be filled with part of the product contained in the medical container.

Description of Related Art

In this application, the distal end of a component or apparatus means the end furthest from the hand of the user and the proximal end means the end closest to the hand of the user, with reference to the injection device intended to be used with said component or apparatus. As such, in this application, the distal direction is the direction of injection with reference to the injection device, and the proximal direction is the opposite direction, i.e. the direction of the transfer of the product from the vial to the injection device. In the present application, "longitudinal" means aligned on the axis defining the distal and proximal directions as defined above.

One of the ways to improve health is to immunize entire populations against a number of diseases. To date, injection administration is the most common method of administering vaccines.

Each year, numerous drugs, for example vaccines, are prepared by healthcare institutions for distribution throughout many parts of the world, including those locations in cities, villages or remote area.

From a supply chain perspective, an efficient vaccine packaging is a multidose container such as a multidose vial, that is to say, a vial that may contain up to 10, 100 or 1000 doses of vaccine, one dose being intended for one patient. These vials are usually closed by a septum. In preparation of an injection of a vaccine, the user pierces the septum of the vial with the needle of an empty syringe, the user then fills the syringe with one dose of vaccine and proceeds to the injection of the vaccine to the patient.

In locations where it is difficult to maintain favorable hygienic conditions such as remote locations which are far from towns and from hospital facilities, the multidose vials may be handled and manipulated at ambiant air. In such cases, the septum of the vial may be contaminated either by the ambiant air, or, each time a dose of vaccine is removed, by the needle of the empty syringe used.

In addition, in regions where there is limited or potentially no supply of energy to power cooling equipment, such as a refrigerator, the multidose vials may be maintained in cold conditions by simple contact with ice packs. As time goes by, part of the ice may melt and turn into water, and the septum of the multidose vials may be in contact with such water that may contaminate the septum of the vial.

It may then be the case that a multidose medical container, such as, for example, a 10-dose medical container, is opened and that only three doses are used, for vaccinating three patients only. The remaining content of the medical container is then wasted because it is not administered in a sufficiently short time after opening of the medical container and the vaccine or drug sterility cannot be guaranteed.

Vaccination campaigns can therefore be made difficult in some regions and a significant proportion of vaccines may be wasted. This has an unacceptable cost to the health organizations in charge of immunization campaigns. In addition, it may happen that in case of vaccination campaigns, or pandemic, hundreds of patients need to be vaccinated in a very short time which complicates the management of product doses and the patient track record.

As such, multidose vials imply that the septum of the vial be pierced successively a high number of times, namely as many as the number of doses present in the vial. In order to ensure safe injections, the sterility of the vial content and the integrity of its septum should be maintained during the whole time the vial is used.

Successive piercings of the same septum area could lead to the contamination of the vial interior by introducing contaminants inside the vial from the first piercing of the septum. Moreover, different piercings can form a definitive hole through the vial septum, the septum being incapable of resealing after several piercings in the same area and therefore losing its isolating properties that ensures the integrity of the vial content from the outside environment.

Therefore, it would be desirable to provide a device that would allow several successive piercings of a multidose vial septum and that would guaranty that said piercings be carried out in aseptic conditions. In particular, it would be desirable to provide a device that would guaranty that each new piercing be completed in an area of the septum that has not yet been pierced during the previous withdrawals of doses of product.

SUMMARY OF THE INVENTION

A first aspect of the present invention is an adaptor for coupling with a medical container filled with a number N of doses of a product to be withdrawn therefrom, said medical container being closed by a septum, said septum having an outer surface intended to be submitted to at least N successive needle piercings for completing withdrawal of said N doses of product, the adaptor comprising:
 a gripping member for securing the adaptor to the medical container, said gripping member including at least one needle access port,
 marking means coupled to said needle access port, for designating to a user a not yet pierced area of said outer surface, for completing the next of said N successive piercings.

The adaptor of the invention is intended to be mounted on a medical container, such as for example a conventional vial for storing pharmaceutical products, such as multidose vials for vaccines. Such a vial 1 is shown on FIGS. 1A-1C and generally comprises a tubular barrel 2 having a longitudinal axis A, closed at an end and having a collar 3 at the opposite end, said collar 3 being closed by a septum 4. Usually, the septum 4 is fixedly attached to the collar 3 of the vial 1 by a peripheral band 5, said peripheral band 5 leaving a part of the septum 4, herein called outer surface 4a of the septum, directly facing the outside of the vial 1, namely the outside environment. The septum 4 is usually made of a material impermeable to gas and liquid and it seals hermetically the content of the vial 1. The septum 4 is also pierceable by a needle of an injection device intended to be filled with the product contained in the vial, said septum 4 being accessible to said needle via its outer surface 4a.

In the present application, "pierceable" means that the septum, or elastomeric piece, of the adaptor may be pierced and traversed by the needle of an injection device such as a syringe, an auto-injector, or a reconstitution device, for example for administering a pharmaceutical product such as a drug or a vaccine.

The gripping member of the adaptor of the invention may be any member capable of securing the adaptor on the medical container, and in particular around the collar of the medical container, either in a temporary or permanent way. The needle access port is preferably intended to face the outer surface of the septum when the adaptor is coupled to the medical container.

The adaptor of the invention allows piercing the septum of the medical container in good hygienic conditions multiple successive times, in particular at least N successive times, N corresponding to the number of doses of product contained in the medical container. Indeed, when the user decides to fill an empty syringe with a dose of drug contained in the medical container, the user simply secures the adaptor of the invention on the medical container by means of the gripping member. Due to the markings means, the user can determine, each time the user wishes to proceed with the withdrawal of a dose of product, where to prick the needle in order to pierce the outer surface of the septum at a location where it has not yet been pierced, and therefore at a location where it is still sterile, despite the previous potential piercings that have been completed in relation with the previous withdrawals of product doses.

The user may repeat the piercing step with the needle of a new empty injection device until all the doses contained in the medical container are removed. For each piercing, the user is ensured to pierce the septum at a location where it has not been contaminated by previous piercings. Successive piercings of the same septum area are therefore prevented and the integrity of the septum is maintained during the whole time the medical container is used. Moreover, the sterility of the inside of the vial is also maintained as potential contaminants are blocked by the vial septum.

In certain embodiments, the adaptor may be provided with a closure member for closing said needle access port in a storage position of said adaptor. The closure member allows preserving the sterility of the needle access port before the use of the adaptor, and is to be removed in order to proceed with withdrawals of doses of product.

In certain embodiments, said needle access port comprises at least one substantially longitudinal passage way open at both its proximal and distal ends for access by the needle, said distal end facing said outer surface of the septum when said adaptor is coupled to said medical container.

In certain embodiments, said marking means comprise at least N membranes stuck to each other, each membrane substantially closing said proximal end of said substantially longitudinal passage way and being provided on its outer wall with one opening for directing the needle towards said not yet pierced area of said outer surface. In certain embodiments, the N membranes are removable one after the other.

For example, the marking means are made of a pile of N sterile labels stuck to each other, and removable one after the other and for example one at a time. In embodiments, each label may be provided on its outer wall with only one opening. In such a case, this opening indicates to the user the place where to introduce the needle for the next piercing. Alternatively, each label may be provided with several openings, only one of said openings indicating to the user the place where to introduce the needle for the next piercing, the other openings corresponding for example to previous piercings. In such a case, the opening intended to indicate to the user the place where to introduce the needle for the next piercing may preferably be marked appropriately so that the user easily recognizes it.

For example, before the first withdrawal, the top label may be named "Label N" meaning that N doses still remain in the medical container, and may have only one opening designed on its outer wall. For proceeding to the first withdrawal of a dose of product, the user introduces the needle in said opening, pushes the needle distally, pierces the outer surface of the septum at a first location and withdraws a dose of product. Once this first withdrawal of product is completed, the user removes the label "Label N". A next sterile label appears, for example named "Label N-1", thereby informing the user that (N-1) doses of product still remain in the container. Label N-1 may have only one opening designed on its outer wall, but at a different location with respect to that of the former Label N. As a consequence, for proceeding to the next withdrawal of product, the user introduces the needle in the opening of Label N-1. By pushing the needle distally, the user automatically pierces the outer surface of the septum at a location different from the first location.

The marking means may therefore provide the user with information about the number of doses remaining in the medical container.

Alternatively, Label N-1 may have two openings designed on its outer wall, one corresponding to the opening of Label N, and a new opening, intended to indicate to the user the place where to introduce the needle for the next piercing. In such a case, the new opening may, for example, be marked by a visible circle, so that the user directly differentiates it from the opening of the previous piercing.

In certain embodiments, the adaptor further comprises guiding means for forcing the needle towards a specified location of said not yet pierced area. For example, said substantially longitudinal passage way is provided with N separate substantially longitudinal channels, said N separate substantially longitudinal channels forming at least part of said guiding means.

For example, the distal end of each channel faces a dedicated part of said not yet pierced area when said adaptor is coupled to said medical container, and the proximal end of each channel faces only one of said openings provided by said N membranes, said N separate substantially longitudinal channels forming at least part of said guiding means.

In particular, as the longitudinal channels are separated, and in particular separated and isolated from each other, each channel preserves its sterility independently from the others. This allows avoiding contamination of the needle of the drug delivery device when introduced in the adaptor. This also gives an additional protection against contaminants reaching the inside of the vial and contributes to maintaining the efficacy of the product contained in the medical container over an extended period of time.

In such embodiments, the needle is forced to a dedicated pathway, namely the channel, within the needle access port, for each piercing, each dedicated pathway being different from a piercing to the other. As a consequence, for each piercing, the needle is forced to reach the outer surface of the septum at a location which has not been reached previously. The piercing of the outer surface of the septum in a not yet pierced area is therefore ensured. In addition, the sterility of each channel is preserved, as it has not yet been used.

In embodiments, the adaptor further comprises a pierceable elastomeric piece lodged within said needle access port, and intended to face said outer surface of said septum when said adaptor is coupled to said medical container.

The pierceable elastomeric piece of the adaptor in accordance with an embodiment of the invention has preferably a part intended to be in contact with the outer surface of the septum when said adaptor is secured on said medical container. In other words, the elastomeric piece has a design, shape, and location in the needle access port of the adaptor, allowing a part of it to be in contact with the outer surface of the septum when said adaptor is secured on said medical container.

In embodiments, the elastomeric piece is made of a gas and liquid impermeable material capable of flexing under pressure. For example, the elastomeric piece has a thickness ranging from 1 to 8 mm, preferably from 2 to 4 mm. The elastomeric piece may show a hardness ranging from 10 to 100 Shore A, preferably from 40 to 70 Shore A, measured according to standard DIN 53505.

Suitable materials for the pierceable elastomeric piece of the adaptor of the invention include natural rubber, acrylate-butadiene rubber, cis-polybutadiene, chloro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

In certain embodiments, the pierceable elastomeric piece is self-resealing. In the present application, "self-resealing" means that the elastomeric piece automatically and rapidly closes the hole produced by the piercing of the needle, for example in less than 0.5 seconds, once the needle is removed from the elastomeric piece. This automatic closure step may occur a high number of times, for example as many times as necessary for removing the numerous doses of products contained in the multidose medical container. This automatic obstruction reduces or prevents air and/or contaminants from entering inside the medical container, and thus allows asepsis maintenance. Moreover, the presence of the pierceable elastomeric piece of the adaptor of the invention gives time to the septum of the medical container to reseal, as the needle is still present in the pierceable elastomeric piece after it is removed from the septum. As such, neither air nor contaminants may be introduced in the medical container, even if the medical container is maintained under negative pressure after the removal of one or more doses of product. In addition, the septum of the medical container may itself be self-resealing.

Suitable materials for self-resealing pierceable elastomeric piece of the adaptor of the invention include synthetic polyisoprene, natural rubber, silicone rubber, thermo-plastic elastomers, or the like or a combination thereof.

Once the adaptor is secured on the medical container, the pierceable elastomeric piece, when present, is in contact with the outer surface of the septum of the medical container. As a consequence, introducing the needle in the medical container implies that the needle pierces and traverses the elastomeric piece before piercing the septum. During this step, the needle mechanically rubs against the material forming the elastomeric piece and it is naturally cleaned, as the potential bacteria are wiped out from the needle when said needle penetrates the elastomeric piece. In addition, once the needle protrudes out of the elastomeric piece of the adaptor, it directly enters the septum of the medical container and may therefore not be contaminated by foreign elements.

In another embodiment, an adaptor for coupling with a medical container filled with a number N of doses of a product to be withdrawn therefrom is provided. As discussed previously, the medical container is closed by a septum having an outer surface intended to be submitted to at least N successive needle piercings for completing withdrawal of the N doses of product. The adaptor includes a gripping member that secures the adaptor to the medical container. The gripping member includes at least one needle access port. The adaptor also includes at least N membranes stuck to each other. Each membrane substantially closes the at least one needle access port and is configured to designate to a user a not yet pierced area of the outer surface of the septum for completing the next of the N successive piercings.

Another aspect of the present invention is an assembly comprising a medical container filled with a number N of doses of a product to be withdrawn therefrom, said medical container being closed by a septum, said septum having an outer surface intended to be submitted to successive needle piercings for completing withdrawal of doses of product, and an adaptor as described above. For example, the outer surface of the septum is intended to be submitted to at least N successive needle piercings for completing withdrawal of said N doses of product.

BRIEF DESCRIPTION OF THE DRAWINGS

The present invention will now be described in greater detail based on the following description and the appended drawings in which:

FIGS. 1A-1C are respectively a perspective view, a partial side view and a partial cross section view of a conventional vial on which the adaptor of the invention is to be mounted, FIGS. 2A-2D are respectively a perspective view, a bottom view, a top view, and a cross section view along plane I-I' of FIG. 2C, of an embodiment of the adaptor of the invention, FIG. 3A is a top view of the marking means of an embodiment of the adaptor of the invention, FIG. 3B is a perspective view of a label forming a part of the marking means of FIG. 3A, FIGS. 4A-4B are respectively a perspective view and a cross section view of the adaptor of FIGS. 2A-3B once coupled to a medical container of FIGS. 1A-1C, before use, FIGS. 5A-5B are respectively a perspective view and a perspective cross section view of the adaptor and medical container of FIGS. 4A-4B, in use, when two doses of product remain in the medical container.

DESCRIPTION OF THE INVENTION

Figure 6A:
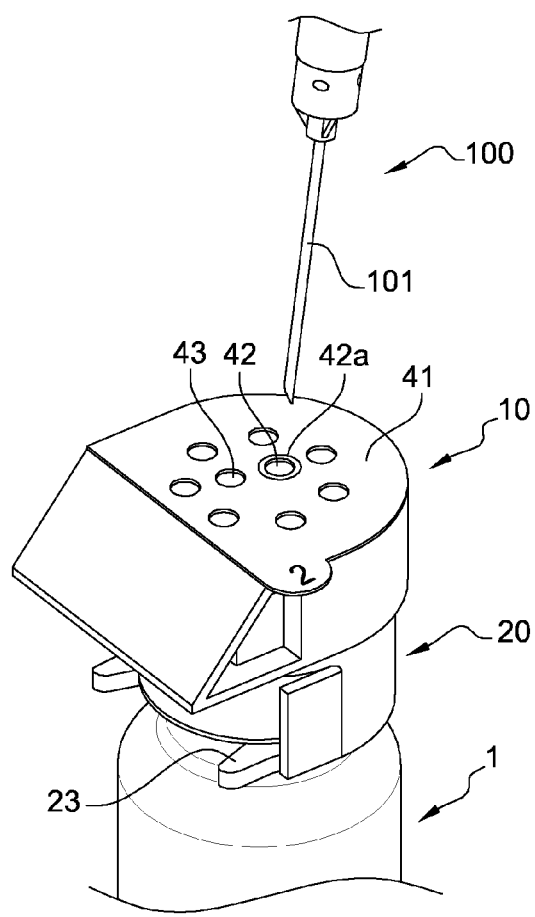
FIG. 6A is a partial perspective view of the adaptor and medical container of FIG. 5A before withdrawing the ninth dose of product.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

While the present invention is described with reference to several distinct embodiments of an adaptor for a multidose medical container and method of use, those skilled in the art may make modifications and alterations without departing from the scope and spirit. Accordingly, the above detailed description is intended to be illustrative rather than restrictive.

With reference to FIGS. 4A-4B is shown an adaptor 10 in accordance with a first embodiment of the invention, coupled on a medical container, such as a multidose vial 1 as shown on FIGS. 1A-1C.

In the example shown on FIGS. 1A-6C, the vial 1 is filled with ten doses of product. The outer surface 4a of the septum 4 is therefore intended to be submitted to ten successive piercings of a needle for withdrawing the ten doses of product one after the other. In examples not shown, the vial could be filled with five doses of product, or twenty doses, or one hundred doses. In such cases, the septum 4 would be intended to be pierced successively five times, respectively twenty or one hundred times. Although the description below relates to a ten-doses vial 1, it applies to any vial filled with N doses of product.

The adaptor 10 comprises a gripping member 20 intended to secure the adaptor 10 onto the vial 1, at least one needle access port 30 for allowing the needle of an injection device (see FIG. 6C) to reach the septum 4, and marking means, under the form of a stack 40 of ten labels 41, for designating to a user a not yet pierced area of the outer surface 4a of the septum 4, when the user is ready to complete one of the ten successive piercings required for withdrawing the ten doses of product.

With reference to FIGS. 2A-2D, the gripping member 20 and the needle access port 30 will now be described in detail.

The gripping member 20 comprises a U-shaped body 21, having a partially tubular wall 22 showing a height suitable for surrounding the collar 3 of the vial 1 (see FIG. 4A), with two free ends 22a corresponding to the ends of the branches of the U, the U-shaped body 21 therefore forming a clipping member. Each free end 22a is provided with a distal front projection forming a radial rim 23.

Proximally with respect to the U-shaped body 21, the gripping member 20 is further provided with a solid body 24 pierced in its central area by a needle access port 30 as shown on FIG. 2D. On the example shown, the needle access port 30 has the global shape of a substantially longitudinal passage way open at both its proximal end 30a and at its distal end 30b, under the form of ten separate substantially longitudinal channels 31. By substantially longitudinal, it is meant in the present application, that the passage way and the channels 31 are substantially aligned on longitudinal axis A, but may slightly divert from this longitudinal axis by a light angle, as long as they allow a needle to traverse the solid body 24 in view of reaching the outer surface 4a of the septum 4 (see for example FIG. 6C). As such, on FIG. 2D, where only two of the ten longitudinal channels 31 are visible, one can see that the longitudinal channels 31 are slightly oblique with respect to longitudinal axis A. As a result, in this example, the passage way of the needle access port 30, which encompasses the ten longitudinal channels 31, has globally a conical shape.

Figure 8:
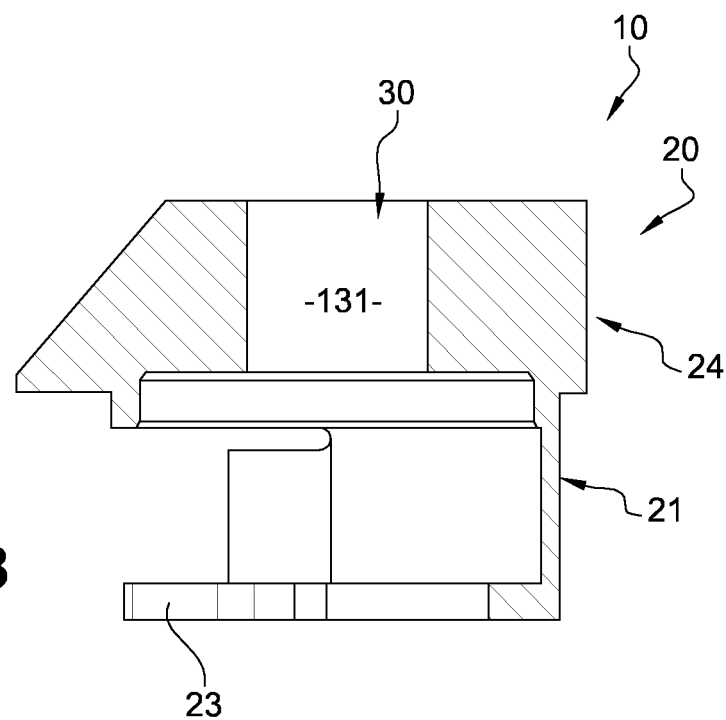
FIG. 8 is a cross section view of another embodiment of the gripping member of the adaptor of the invention.

In another embodiment, as shown on FIG. 8, the longitudinal passage way of the needle access port 30 does not include a plurality of separate longitudinal channels but is under the form of a cylindrical conduct 131, the diameter of which is equal or less than the diameter of the outer surface 4a of the septum 4 of the medical container the adaptor is intended to be coupled with. On this Figure, the references designating the same elements as in FIGS. 2A-2D have been maintained.

In the example shown on FIGS. 2A-2D, the solid body 24 is further provided with a projection 25 provided with a surface 25a for storing information for example.

In the example shown on FIG. 2D, the gripping member 20 further comprises a pierceable elastomeric piece 60 lodged within the needle access port 30. The pierceable elastomeric piece 60 is located in a distal region of said needle access port, so that it faces the outer surface 4a of the septum 4 when the adaptor 10 is coupled to the vial 1 (see FIG. 4B).

The pierceable elastomeric piece 60 has globally the shape of a flat cylinder and is dimensioned and shaped so as to be received within the distal region of the passage way of the needle access port 30 with friction. The pierceable elastomeric piece 60 is made of a material impermeable to gas and liquid capable of flexing under pressure.

Suitable materials for the pierceable elastomeric piece 60 of the adaptor of the invention include natural rubber, acrylate-butadiene rubber, cis-polybutadiene, chloro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

Preferably, the elastomeric piece is self-resealing and it automatically seals the hole produced by the piercing of the needle, automatically and rapidly, for example in less than 0.5 seconds, once the needle is removed from the elastomeric piece. This automatic closure step may occur a high number of times, in particular as many times as necessary for removing the product doses initially present in the multidose vial 1. Indeed, it is particularly valuable to prevent air from the outside to enter into the vial. In this way, the product contained inside the multidose vial, for example a pharmaceutical drug, is kept sterile and the inside of the vial is kept under negative pressure during the whole time of use of the vial. Suitable materials for self-resealing pierceable elastomeric piece include synthetic polyisoprene, natural rubber, silicone rubber, thermo-plastic elastomers, or the like or a combination thereof.

With reference to FIG. 3A is an upper view of a stack 40 of ten labels 41. On FIG. 3A, only one label, the top label 41, is visible. The other nine labels are stuck one to each other and to the top label 41, the ten labels 41 being removable from the stack 40 one by one.

The top label 41 has the figure "10" provided on it, thereby informing the user that ten doses are remaining in the vial. The top label "10" has one opening 42 designed on its outer wall, marked with a circle 42*a*, for indicating to the user where to introduce the needle of a drug delivery device, in view of proceeding to the first withdrawal of product.

In other embodiments not shown, the top label 41 has the figure "1" on it, to inform the user that he is about to withdraw the first dose of product.

With reference to FIG. 3B, one of the other nine labels 41 is shown on its own, once removed from the stack 40. On this Figure, digit "3" is provided on the label 41, thereby meaning that three doses are left in the vial 1. As shown on this Figure, the label 41 named "3" comprises eight openings drawn on its surface. Seven of these openings are unmarked openings 43, and one of these openings is a marked opening 42, provided with a circle 42*a*. The marked opening 42 delimits the location where the user needs to complete the next piercing with the needle in order to reach a not yet pierced area of the outer surface 4*a* of the septum when the adaptor 10 is in use. In particular, the marked opening 42 designates a corresponding longitudinal channel 31 which has not been used yet and which is therefore sterile. As each channel 31 is used only once, the needle of the drug delivery device is prevented from being in contact with any contaminated area.

In the adaptor 10 of the invention, in a before use position as shown on FIG. 4A-4B, the stack 40 of ten labels 41, is positioned onto the top surface of the solid body 24 so as to substantially close the proximal end 30*a* of the needle access port 30. In particular, to the proximal end of each longitudinal separate channel 31, corresponds a marked circle 42 of one of the ten labels 41. In addition, on the example shown, each label 41 closes the proximal ends of longitudinal channels that have not been used yet, thereby preserving the sterility of each not yet used longitudinal channel 31.

With respect to FIGS. 4A and 4B, the top label 41 with the digit "10" is covered with a closure member 50 under the form of a sticker, in order to preserve the sterility of the needle access port in the storage position of the adaptor. On these Figures, the adaptor is coupled to the vial 1. In this view, the gripping member 20 has been mounted on the collar 3 of the vial 1 in a sliding way, and the radial rims 23 now surround said collar 3, thereby securing the adaptor 10 on the vial 1. In this coupled position of the adaptor 10 on the vial 1, the needle access port 30, in which is lodged the pierceable elastomeric piece 60, is aligned on the outer surface 4*a* of the septum 4 of the vial 1. The pierceable elastomeric piece 60 may be in tight contact with the outer surface 4*a* of the septum 4 leading to a close interface between the elastomeric piece 60 and the septum 4.

In particular, in this position of the adaptor 10 coupled to the vial 1, the distal end of each longitudinal channel 31 faces a dedicated area of the outer surface 4*a* of the septum 4, and the pierceable elastomeric piece 60 faces the outer surface 4*a* of the septum 4.

For proceeding to the first product withdrawal, the user removes the closure member 50. The top label 41 named "10" of FIG. 3A appears. The user introduces the needle of a drug delivery device in the marked opening 42. Since the marked opening 42 of label "10" corresponds to the proximal end of only one longitudinal channel 31, the needle is forced to a dedicated area, hereinafter called first location, of the outer surface 4*a* of the septum 4, after having pierced the pierceable elastomeric piece 60.

The user withdraws a dose of product and removes the needle of the drug delivery device.

The user then removes label "10" and label "9" appears, with two openings designed on its outer wall, only one of these two openings being a marked opening. The user may repeat this step nine times until reaching the last label with the digit "1".

In another embodiment (not shown), the digit printed of each label corresponds to the number of doses already withdrawn. The first label of the stack therefore displays the digit "1" and the last label of the stack displays the digit "10".

With respect to FIGS. 5A to 6C, such a step is detailed, starting from the time the user has removed the needle after having proceeded to the eighth withdrawal, as shown on FIGS. 5A-5B. On these Figures, Label "3" is still present, and one can see in which opening the eighth withdrawal has been completed, namely in the marked opening 42. Label "3" is also provided with the seven openings 43 corresponding to the previous piercings. Label "3" still closes the proximal ends of two longitudinal channels 31 which have not yet been used: one these channels 31*a*, is visible in FIG. 5B.

The user then removes Label "3" by pulling it out in the direction of arrow F shown on FIG. 5A. Label "2" appears as shown on FIG. 6A, with a marked opening 42, indicating to the user the area where to introduce the needle for the next piercing. This opening 42 corresponds to the proximal end of the channel 31*a* of FIG. 5B. Channel 31*a* is therefore sterile. In addition, one can see on Label "2", that former marked opening 42 of Label "3" has become an unmarked opening 43 on Label "2".

Figure 6B:
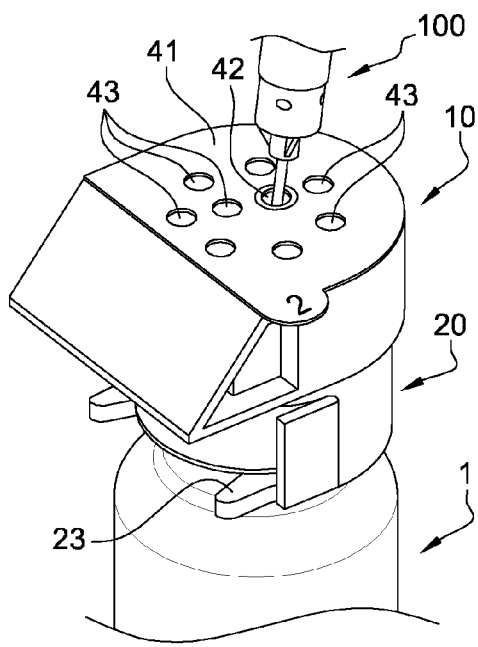
FIGS. 6B and 6C are respectively a partial perspective view and a cross section view of the adaptor and medical container of FIG. 6A during the withdrawal of the ninth dose of product.
Figure 6C:
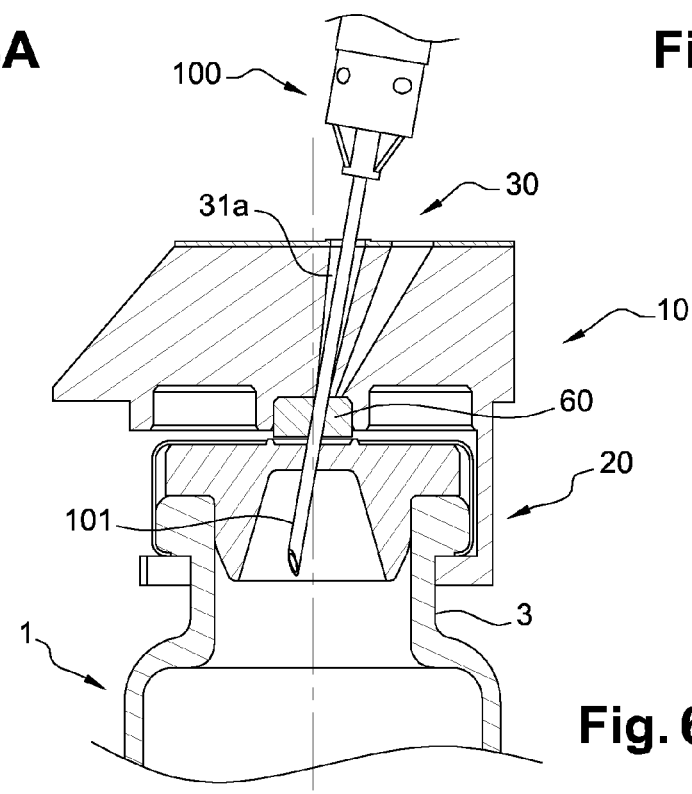

As shown on FIGS. 6B and 6C, the user then introduces the needle 101 of a drug delivery device 100 into marked opening 42 of Label "2". The needle 101 is forced to follow the longitudinal channel 31*a* towards the pierceable elastomeric piece 60 and towards a not yet pierced area of the outer surface 4*a* of the septum 4. The longitudinal channel 31*a* therefore acts as guiding means for forcing the needle 101 to a specified location, different from the first and subsequent second to eight locations, of the not yet pierced area of the outer surface 4*a* of the septum 4.

The user then withdraws the ninth dose of product and removes the needle 101 out of the vial 1. For proceeding to the tenth withdrawal of product, the user removes Label "2" and introduces the needle of a new drug delivery device into the marked opening of Label "1".

The labels 41, the openings 42 and the circle 42*a* form marking means for designating to a user a not yet pierced area of the outer surface 4*a* of the septum 4. This allows prevention of successive piercings of the septum at the same area, which would damage the septum by forming a definitive hole and then would provide a direct access for the outside contaminants to enter into the vial. As a result, the isolation function of the septum is maintained between the vial interior and the outside environment and the contamination of the vial interior is prevented.

Moreover, in the example shown, these marking means also integrate a dose counting system by showing the number of doses remaining into the vial without a specific additional action from the user. Alternatively, these marking means may integrate a withdrawal counting system by showing the number of doses already withdrawn from the vial, without a specific additional action from the user.

In addition, the stack 40 of labels 41 maintains the sterility of each longitudinal channel 31*a* and reveals a not-yet-used and sterile channel for each dose withdrawal. During the dose withdrawal, the needle of the drug delivery device only contacts sterile areas and is not contaminated by bacteria, viruses or other contaminants from the outside environment. As a result, the product efficacy is maintained over an extended period of time which allows to withdraw doses from an opened vial during a significantly long period of time, and reduces wastage of unused doses.

In certain embodiments, the adaptor of the present invention may be provided with a time monitoring system (not shown). Indeed, the content of the vial may be considered contaminated after a limited period of time i.e. 28 or 30 days. Therefore, a time monitoring system may be added to the adaptor in order to monitor the elapsing time from the first dose withdrawal or to indicate what is the time remaining before the, for example, 28 or 30 days deadline.

This time monitoring system could be an electronic timer or a system based on the diffusion of fluid into a reservoir. For example, the elapsing or remaining time can be monitored by the kinetics of ink progression in a microfluidic circuit. Such a system is particularly attractive because it is small and reliable. For example, such a system could be integrated onto a section of a dose counting system or onto the surface 25a of projection 25 of the present adaptor (see FIG. 2A). Such a time monitoring system is commercially available under, for example, the Timestrip® trademark from Timestrip UK Ltd. Such a system could prevent the injection of potentially expired vaccines or drugs to patients, but could also avoid wastage of valuable drugs and vaccines by encouraging the use of the first opened vials.

Figure 7:
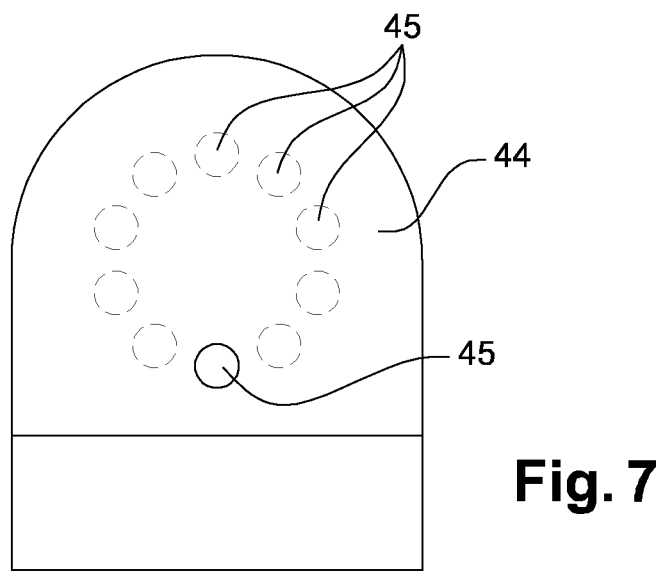
FIG. 7 is a top view of another embodiment of the marking means of the adaptor in accordance with an embodiment of the invention.

In certain embodiments, each label may be provided with only one opening. The user does not need to differentiate a marked opening from an unmarked one, as only one opening is present. With reference to FIG. 7, is shown an example of such an embodiment. In the Figure, only the top label 44 is visible, with its only opening 45. The openings 45 of the other labels 44, which are stuck together and to the top label 44, are shown as a dotline. Each label 44 has only one opening 45 designed on its outer wall. The labels 44 of FIG. 7 may for example be used with the adaptor 10 of FIG. 8.

Figure 9A:
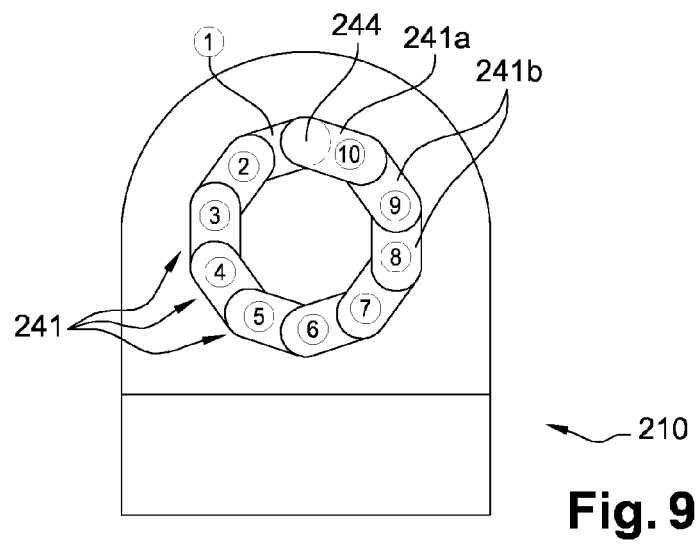
FIGS. 9A-9C are top views of the marking means of another embodiment of the adaptor of the invention.
Figure 9B:
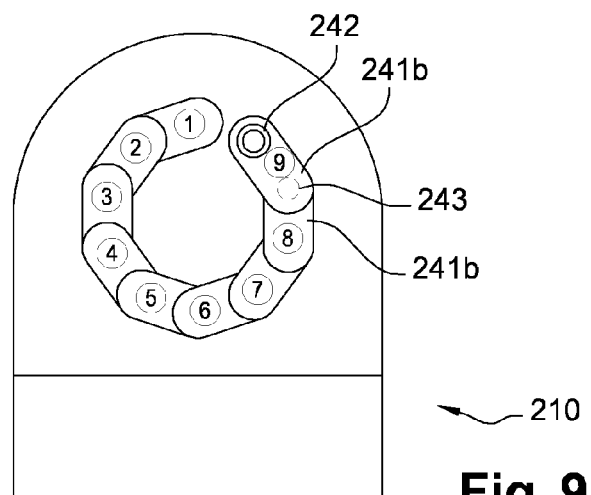
Figure 9C:
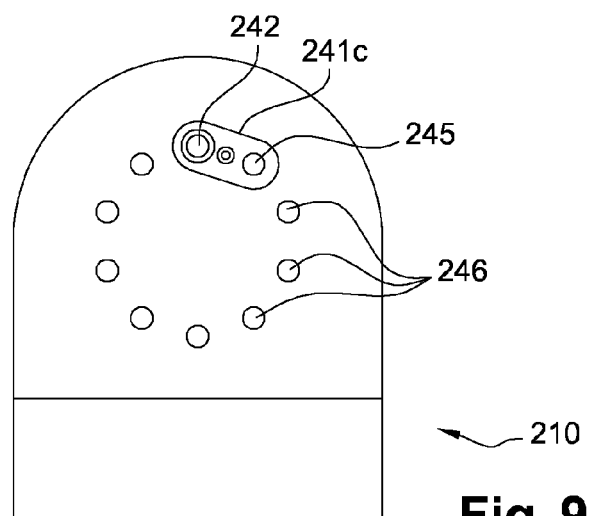

In another embodiment of the invention shown in FIGS. 9A-9C, the adaptor 210 comprises labels 241 in a circular arrangement. Each label 241 only covers two openings 242, one being closed and one being opened, as explained below. The size of the labels 241 is smaller than the size of labels 41 of the adaptor 10 according to the first embodiment of the invention. Each label 241 has an extremity 244 which is not provided with adhesive and which freely extends above the adaptor 210, therefore forming a peeling tongue.

The top label 241a named "10" in FIG. 9A has no opening and does not give access to the outer surface 4a of the septum 4. To proceed with the withdrawal of the first dose, the user removes the label 241a named "10" by grasping the extremity 244 and pulling it out. The label "9" is now completely visible, as shown in FIG. 9B. It gives access to a marked opening 242 and closes the next opening 243 (visible in dotted line in FIG. 9B for sake of understanding), which is not yet visible by the user. The marked opening 242 indicates to the user the area where to introduce the needle to perform the first product withdrawal.

The user then proceeds in a similar way with the other labels 241b to withdraw the next doses of product, up to the last label named "0", as shown in FIG. 9C and similarly to the adaptor 10 of the first embodiment described above.

In FIG. 9C, only the last label 241c named "0" remains on the adaptor 210, at the exact place of the first label "10". This label is fully provided with adhesive and does not comprise any peeling tongue. It gives access to the last marked opening 242 and indicates to the user where to introduce the needle to withdraw the last dose of product. It also comprises an unmarked opening 245 which has been used to withdraw the first dose of product. The other openings 246 which have been used to withdraw the subsequent dose of product are now all opened, but unmarked, in order to prevent the user to use twice the same opening.

The adaptor 210 according to this embodiment of the invention can be produced by a simple manufacturing process, since only three different types of labels are required: a first type 241a with no opening, a second type of label 241b with a single marked opening and a third type of label 241c with a marked opening and an unmarked opening. In another embodiment of the invention, the third type of label 241c can be printed at the surface of the adaptor 210, therefore reducing the production of labels to the first and second types only. Finally, the assembly of the labels 241 on the adaptor 210 can be fast as an accurate positioning of each label 241 onto the adaptor 210 is not required.

The adaptor of the present invention, in particular with a dose counting system, gives a quick information to the user on the content of the multidose vial.

The adaptor of the invention also allows safe and sterile successive withdrawals of doses of product from a multidose vial. The adaptor of the invention guaranties that successive piercings of the septum of a multidose vial be carried out in aseptic conditions, in particular that each new piercing is completed in an area of the septum that has not yet been pierced during the previous withdrawals of doses of product. The pharmaceutical drug or product efficacy is therefore maintained over an extended period of time. This reduces wastage of valuable drugs as well as non-effective vaccination of populations.

The invention claimed is:

1. An adaptor for coupling with a medical container filled with a number N of doses of a product to be withdrawn therefrom, said medical container being closed by a septum, said septum having an outer surface intended to be submitted to at least N successive needle piercings for completing withdrawal of said N doses of product, the adaptor comprising:
a gripping member to secure the adaptor to the medical container, said gripping member including at least one needle access port; and
marking means coupled to said needle access port, for designating to a user a not yet pierced area of said outer surface of the septum, for completing the next of said N successive piercings, wherein said marking means comprise at least N membranes stuck to each other, each membrane substantially closing said needle access port and being provided on its outer wall with an opening for directing the needle towards said not yet pierced area of said outer surface.

2. The adaptor of claim 1, wherein said needle access port comprises at least one substantially longitudinal passage way open at both its proximal and distal ends for access by the needle, said distal end facing said outer surface of the septum when said adaptor is coupled to said medical container.

3. The adaptor of claim 2, wherein each membrane substantially closes said proximal end of said substantially longitudinal passage way.

4. The adaptor of claim 3, further comprising a guide that directs the needle towards a specified location of said not yet pierced area.

5. The adaptor of claim 4, wherein said substantially longitudinal passage way is provided with N separate substantially longitudinal channels, said N separate substantially longitudinal channels forming at least part of said guide.

6. The adaptor of claim 5, wherein a distal end of each channel faces a dedicated part of said not yet pierced area when said adaptor is coupled to said medical container, and a proximal end of each channel faces only one of said openings provided by said N membranes.

7. The adaptor of claim 1, further comprising a pierceable elastomeric piece lodged within said needle access port, and intended to face said outer surface of said septum when said adaptor is coupled to said medical container.

8. The adaptor of claim 1, further provided with a closure member that closes said needle access port in a storage position of said adaptor.

9. The adaptor of claim 1, further comprising a pierceable elastomeric piece lodged within said needle access port, and intended to face said outer surface of said septum when said adaptor is coupled to said medical container.

10. An assembly comprising:
    a medical container filled with a number N of doses of a product to be withdrawn therefrom, said medical container being closed by a septum, said septum having an outer surface intended to be submitted to successive needle piercings for completing withdrawal of doses of product, and
    an adaptor comprising: a gripping member to secure the adaptor to the medical container, said gripping member including a plurality of needle access ports; and marking means coupled to said plurality of needle access ports, for designating to a user a not yet pierced area of said outer surface, for completing the next of said N successive piercings,
    wherein said gripping member includes a plurality of longitudinal channels disposed between the plurality of needle access ports provided at a proximal end of said gripping member and a portion of the gripping member adapted to be positioned adjacent to said septum.

11. The assembly of claim 10, wherein said needle access port comprises at least one substantially longitudinal passage way open at both its proximal and distal ends for access by the needle, said distal end facing said outer surface of the septum when said adaptor is coupled to said medical container.

12. The assembly of claim 11, wherein said marking means comprise at least N membranes stuck to each other, each membrane substantially closing said proximal end of said at least one substantially longitudinal passage way and being provided on its outer wall with one opening for directing the needle toward said not yet pierced area of said outer surface.

13. The assembly of claim 12, further comprising a guide that directs the needle towards a specified location of said not yet pierced area.

14. The assembly of claim 13, wherein said substantially longitudinal passage way is provided with N separate substantially longitudinal channels, said N separate substantially longitudinal channels forming at least part of said guiding means.

15. The assembly of claim 14, wherein the distal end of each channel faces a dedicated part of said not yet pierced area when said adaptor is coupled to said medical container, and the proximal end of each channel faces only one of said openings provided by said N membranes.

16. The assembly of claim 10, further comprising a pierceable elastomeric piece lodged within said needle access port, and intended to face said outer surface of said septum when said adaptor is coupled to said medical container.

17. The assembly of claim 10, further provided with a closure member that closes said needle access port in a storage position of said adaptor.

18. An adaptor for coupling with a medical container filled with a number N of doses of a product to be withdrawn therefrom, said medical container being closed by a septum, said septum having an outer surface intended to be submitted to at least N successive needle piercings for completing withdrawal of said N doses of product, the adaptor comprising:
    a gripping member that secures the adaptor to the medical container, said gripping member including at least one needle access port; and
    at least N membranes stuck to each other, each membrane substantially closing said at least one needle access port and configured to designate to a user a not yet pierced area of said outer surface for completing the next of said N successive piercings, each membrane being provided on its outer wall with an opening for directing the needle towards said not yet pierced area of said outer surface.

19. The adaptor of claim 17, further comprising a guide that directs the needle towards a specified location of said not yet pierced area.

* * * * *

UNITED STATES PATENT AND TRADEMARK OFFICE
CERTIFICATE OF CORRECTION

PATENT NO. : 10,195,112 B2
APPLICATION NO. : 14/647196
DATED : February 5, 2019
INVENTOR(S) : Frédéric Perot et al.

Page 1 of 1

It is certified that error appears in the above-identified patent and that said Letters Patent is hereby corrected as shown below:

In the Claims

Column 14, Line 44, Claim 19, delete "claim 17," and insert -- claim 18, --

Signed and Sealed this
Fourteenth Day of May, 2019

Andrei Iancu
*Director of the United States Patent and Trademark Office*